United States Patent [19]

Paton et al.

[11] 4,120,291
[45] Oct. 17, 1978

[54] ULTRASONIC SCANNING APPARATUS

[75] Inventors: John Stewart Paton, Beith; Alexander Shaw, Glasgow, both of Scotland

[73] Assignee: Greater Glasgow Health Board, Scotland

[21] Appl. No.: 648,666

[22] Filed: Jan. 13, 1976

[30] Foreign Application Priority Data

Jan. 17, 1975 [GB] United Kingdom ................ 2020/75

[51] Int. Cl.[2] ............................................. A61B 5/00
[52] U.S. Cl. .................................... 128/2 V; 73/618
[58] Field of Search ................ 128/2 V, 2.05 Z, 2.08, 128/24 A; 73/68.5 S, 618

[56] References Cited

U.S. PATENT DOCUMENTS

| | | | |
|---|---|---|---|
| 3,403,671 | 10/1968 | Flaherty et al. | 128/2 V |
| 3,480,002 | 11/1969 | Flaherty et al. | 128/2 V |
| 3,516,401 | 6/1970 | Dell'Aira | 128/2.08 |
| 3,752,255 | 8/1973 | Hill et al. | 73/67.8 S |
| 3,763,463 | 10/1973 | Muir | 128/2 V X |
| 3,974,826 | 8/1976 | Eggleton et al. | 128/2 V |

*Primary Examiner*—William E. Kamm

[57] ABSTRACT

An ultrasonic scanning device having an ultrasonic transmission/reception probe arranged for rapid scanning in a plane while a housing of the device is being held stationary so that real time ultrasonic "pictures" of moving organs such as the heart, can be obtained. The probe is arranged to scan through a window of the housing and mounting means for the probe ensure that ultrasonic signals from the probe have a constant reference point of departure which is at a well-defined small distance from the window. Ultrasonic coupling means are provided between the probe and window, and the window, coupling means and probe may form a subassembly removable from the housing.

10 Claims, 8 Drawing Figures

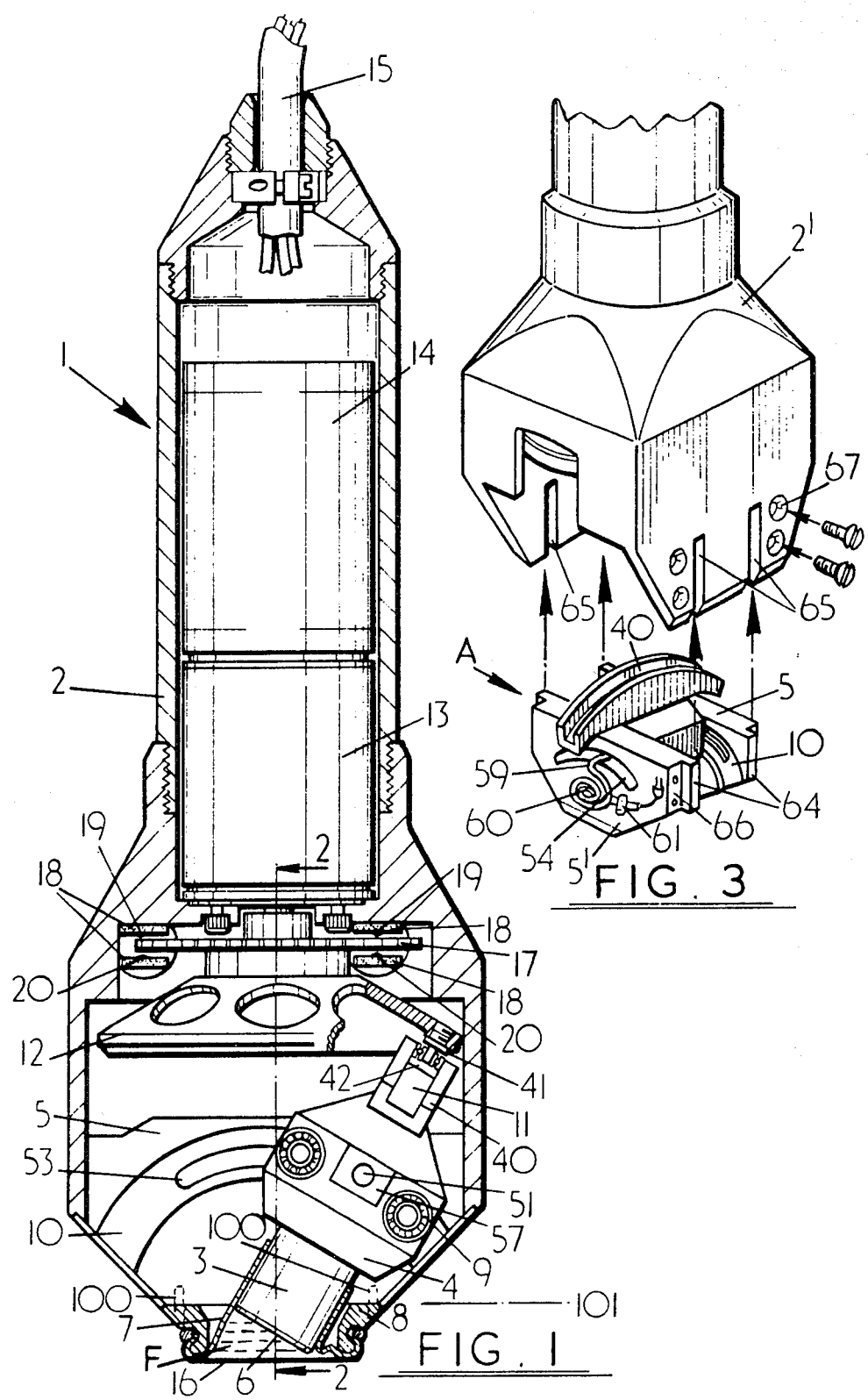

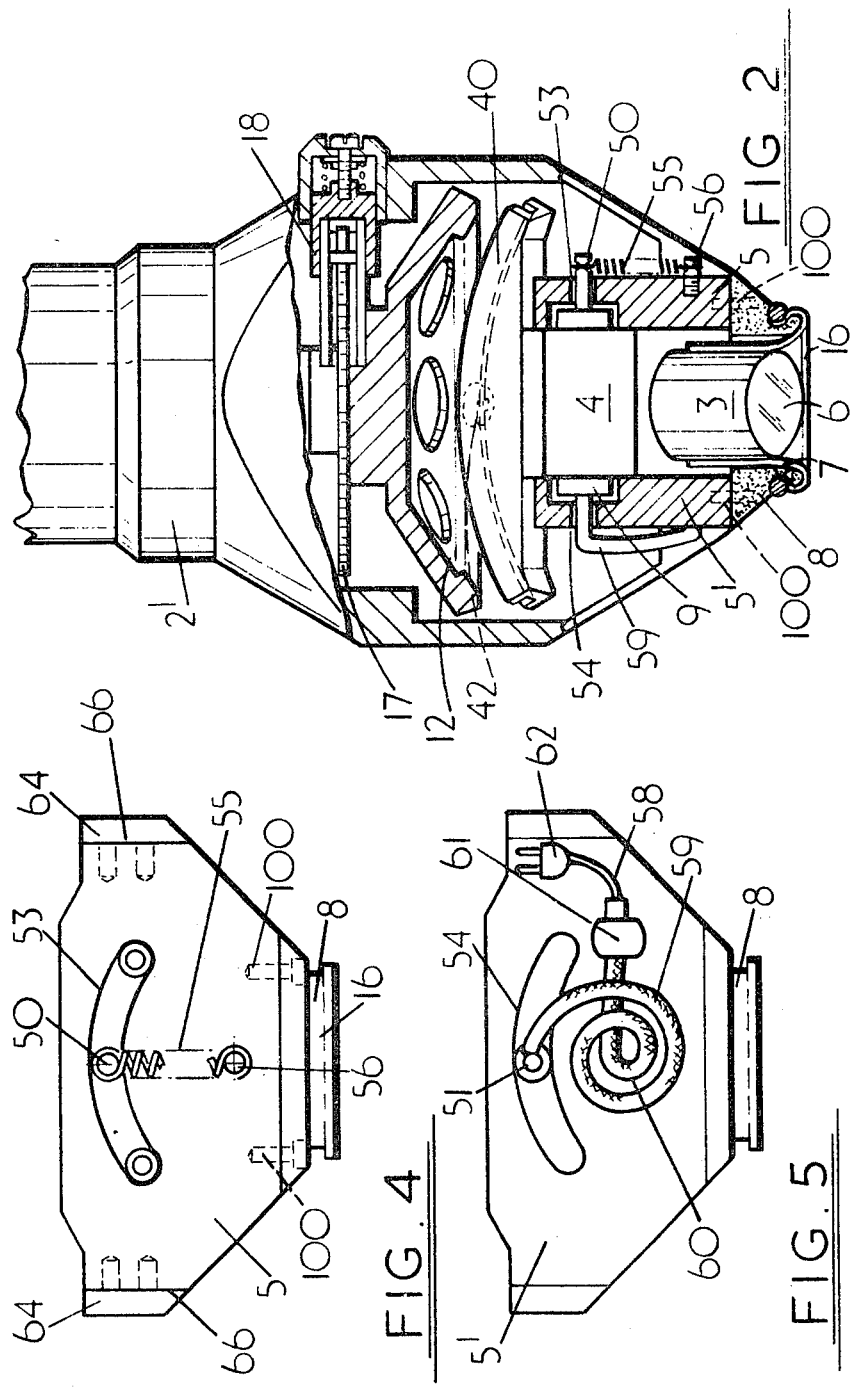

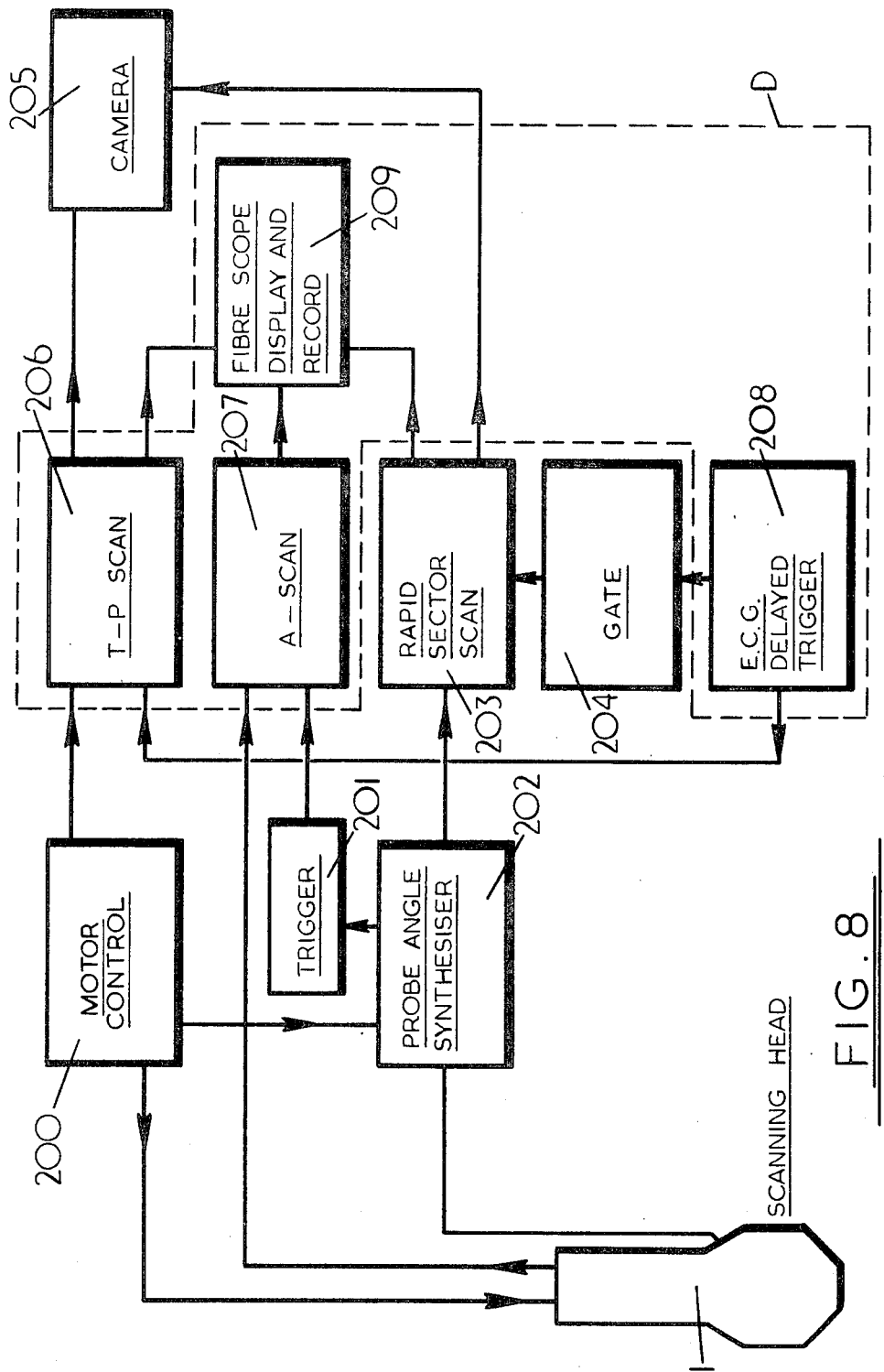

ULTRASONIC SCANNING APPARATUS

This invention relates to scanning apparatus and in particular to an ultrasonic scanning device for use in examining a mass by the transmission and reception of ultrasonic signals and echoes into and from the mass respectively.

In the diagnosis of ailments in human beings, increasing use is being made of ultrasonic transmitting/receiving equipment. In general the devices used have comprised a probe which is moved or scanned manually over a patient's body. In recent times it has been realised that it would provide better results if the scanning could be automated and made more predictable and accurate. This is particularly important where fast scanning is required to provide real-time ultrasonic "pictures" of moving organs such as the heart. Attempts to achieve such fast, accurate and predictable scanning have mainly concentrated on arrays of probes electronically triggered in sequence. Apparatus using such probe arrays are expensive, complicated and have very limited powers of resolution.

It is an object of this invention to provide an improved ultrasonic scanning device.

According to this invention there is provided an ultrasonic scanning device for use in examining a mass by the transmission and reception of ultrasonic signals, the scanning device including a housing, an ultrasonically transparent window of the housing, mounting means secured within the housing, an ultrasonic transmission/reception probe mounted in the mounting means so as to face said window, and means for moving the probe, the mounting means constraining the probe so that the latter can effect only a planar pivoting movement and the moving means being arranged to oscillate the probe between extreme positions of said planar pivoting movement whereby the probe can be pivotably reciprocated in a desired plane while transmitting and receiving ultrasonic signals through said window which can be kept stationary relative to a surface of the mass being examined.

Preferably means are provided for generating electrical signals indicative of the position of the probe relative to said mounting means, said generating means being arranged to produce said signals at a plurality of instants during each cycle of the probe's oscillatory pivoting motion.

In a preferred embodiment a rolling diaphragm is secured to the probe and to the housing around the window, a thin ultrasonically transparent, flexible plastics stretched membrane is secured across said window, a window space is sealingly enclosed by the probe, rolling diaphragm and membrane and a coupling fluid is provided to fill the window space. A sub-assembly of the device may comprise a removable window portion of the housing, the membrane secured across the window portion, the rolling diaphragm secured to the window portion, the probe secured to the rolling diaphragm and the coupling fluid filling said window space, whereby the sub-assembly can be removed from the device and replaced by another such sub-assembly.

Conveniently said moving means includes a motor, a crank connected to the motor, a rolling member pivotably connected to the crank, a carriage carrying the probe and a guide portion of the carriage in which the rolling member is mounted, the carriage being mounted in said mounting means so as to enable said planar pivoting movement of the probe, the rolling member being arranged to roll within said guide portion along an arcuate path defined by the guide portion in a plane of the carriage transverse to the direction of movement of the carriage relative to the mounting means, the motor being arranged to rotate the crank causing in turn the rolling member to roll in said guide portion of the carriage while inducing said planar pivoting movement of the carriage and probe.

Encoding means that may be provided for generating electrical signals indicative of the rotational position of the crank may comprise photo and light-emitting diode pairs and an encoding disc having apertures, the encoding disc being connected to the crank to rotate with the latter, the apertures of the encoding disc being arranged to pass between the diodes of each photo/light emitting duide pair.

Embodiments of this invention will now be described by way of examples only, with reference to the accompanying drawings in which:

FIG. 1 is a vertical partly sectional view of an ultrasonic scanning device embodying this invention;

FIG. 2 is a partly sectional view taken at right angles to the view shown in FIG. 1 along the line 2—2, with a probe of the device moved to the other end of its path of planar pivoting movement;

FIG. 3 is a perspective, exploded view of the device shown in FIG. 1;

FIG. 4 and 5 are respective side views of parts of the device shown in FIG. 1;

FIG. 8 is a block diagram of a scanning system employing the device shown in FIG. 1;

Figure 7:
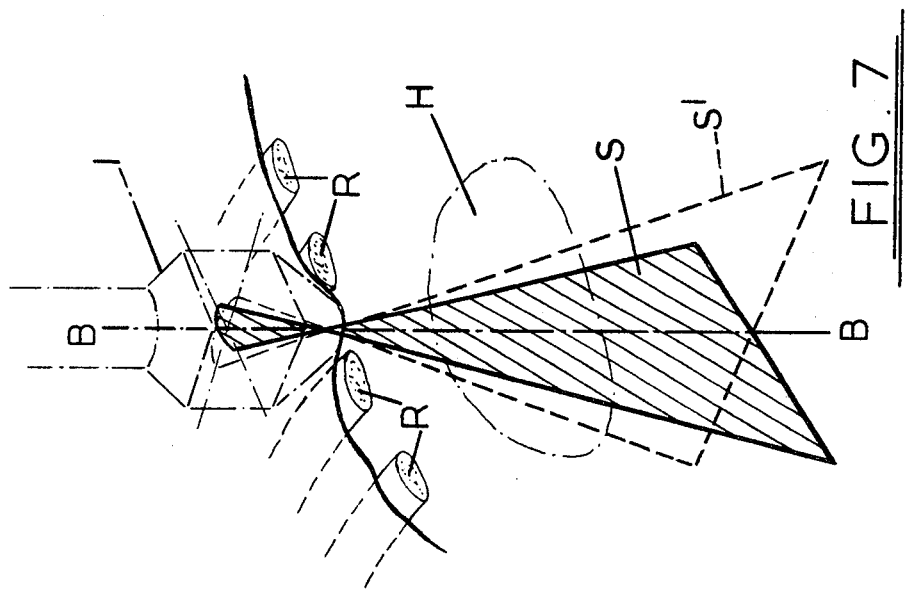
FIGS. 6 and 7 are schematic diagrams illustrating the operation of the device shown in FIG. 1.

Referring to the drawings, an ultrasonic scanning device 1 comprises an elongate housing 2 in which an ultrasonic probe 3 (which may be of any conventional design capable of directional transmission of an ultrasonic pulse and subsequent reception of any echo) is removably mounted in a carriage 4 arranged for planar pivoting movement in mounting means comprising a pair of plates 5 and 5' secured in the housing 2.

The probe 3 has a surface 6 providing transmission and reception of ultrasonic signals and this surface 6 is at one end of a portion of the probe to whose periphery a rolling diaphragm 7 made of rubber is sealingly secured. The rolling diaphragm together with an annular tip portion 8 of the housing, forming an ultrasonically transparent window of the latter over which is stretched a thin flexible plastic membrane 16, form containing means for an acoustic coupling fluid F which is here a rubber-compatible oil, provided in a window space between the surface 6 and the membrane 16.

By "ultrasonically transparent" is meant that the coupling provided by the fluid F and membrane 16 is such as to minimise the setting up of a sharp interface (that would produce a significant echo) when the membrane is placed in contact with the surface of a mass to be examined e.g. in the most relevant case considered here, human skin is the surface to be considered.

The scanning device, the probe 3, rolling diaphragm 7, membrane 16, tip portion 8 and coupling fluid F preferably form a sub-assembly A with a removable window portion of the housing. This is indicated in the drawing by allen screws 100 shown in broken line enabling the window portion of the housing to be secured to the remainder of the latter. The dividing line between the window portion and the remainder of the housing is indicated at 101. The probe 3 is in any case removable from the carriage 4 as mentioned above.

The carriage 4 has roller bearings 9 on either side of its plane of movement and these roller bearings run in an arcuate track formed by guide grooves 10 in the plates 5, 5'. The top of the carriage 4 forms an arcuate guide 40 for a "scotch-yoke" cam generally indicated at 11. The cam 11 is connected to a crank 12 driven by gearing 13 and electric motor 14. The electricity supply for the scanning device is fed in via some of leads 15.

The connection between the crank 12 and guide 40 is provided by a pivot pin 41 screw-threadedly secured at one-end to the crank. The other end of the pivot pin is rotatably mounted in the guide 40 by means of a rolling member in the form of a ball race 42 which is simply pushed into the guide 40 during fitting. The ball race 42 is able to roll within the guide 40 along an arcuate path in a plane of the carriage 4 transverse to the direction of motion of the carriage in the grooves 10. At the same time as this rolling motion takes place the ball race is able to urge the carriage along the grooves.

It is to be noted that the probe 3 is arranged to oscillate about the centre point of the face 6. This is primarily determined by the arcuate track provided by the guide grooves 10 whose curvature is centred on the centre point of the face 6. To ensure clearance between the crank 12 and the guide 40, the latter is provided with an arcuate upper surface whose curvature corresponds to that of the grooves 10 in order that the ball race runs in the guide 40 at a substantially constant depth (the centre of the ball race is substantially equidistant from the centre point of the face 6 at all times).

The carriage 4 has pins 50, 51 projecting outwardly on either side through slots 53, 54 respectively within the grooves 10. The slots 53, 54 extend completely through the plates 5, 5' respectively. The pin 50 is connected by means of a spring 55 to a pivot pin 56 secured to the plate 5. The spring 55 serves to centre the carriage 4 when disconnected from the crank 12 as described below.

Adjacent the pin 51 in the side of the carriage 4 is an aperture 57 through which passes a coaxial lead 58 carrying the electrical signals corresponding to the transmission and reception of ultrasonic signals. The lead 58 extends alongside the pin 51 through the slot 54. Clamped to the pin 51 is one end of a flexible nylon tube 59 through which the lead 58 extends. The nylon tube is formed into a loose spiral 60 adjacent the plate 5' and the other end of the tube 59 is fixed to an anchor plate 61 secured to the plate 5'. The lead 58 is freely slidable within the tube 59 and extends beyond the anchor plate 61 to a fixed plug 62 which can engage a socket (not shown) in the housing as described below. The socket (not shown) is connected to leads 15 in a conventional way.

Thus when the probe 3 is oscillating the lead 58 flexes to and fro with winding and unwinding of the spiral 60, the lead 58 simultaneously sliding to and fro within the tube 59. It has been found that such an arrangement avoids rapid fatigue of the lead 58 due to flexing.

Referring in particular to FIGS. 2-5 there is shown how the sub-assembly A of the device 1 is formed by the plates 5, 5', the carriage 4 (and guide 40), probe 3, diaphragm 7, tip portion 8, membrane 16, coupling fluid F and allen screws 100 of the modified embodiment mentioned above. As can be seen, the ends of the plates 5, 5' are stepped to provide keys 64 which engage slots 65 in an upper housing portion 2' to position the plates 5, 5' accurately and securely. The stepping of the ends of the plates also provides shoulders 66 in which tapped boltholes are formed. Holes 67 in the upper housing portion enables bolts to be inserted to secure the plates 5, 5' and the sub-assembly A as a whole to the upper housing portion. Two lower housing portions (not shown) are removably fitted to the upper housing portion 2' and tip portion 8 to enclose the sub-assembly A. It will now be appreciated that in removing the subassembly the guide 40 simply decouples from the ball race 42 and the fixed plug 62 is automatically extracted from the socket (not shown). A replacement sub-assembly can then be fitted by using the reverse procedure.

Mounted to be rotatable with the crank 12 is an encoder disc 17 associated with photo/light emitting diode pairs 18 to form position-encoding means. The disc 17 has a plurality of apertures through it arranged to pass between a light-emitting diode 19 of each pair 18 and an associated light sensitive or photo diode 20. By "calibrating" the position-encoding means so that certain (at least one) of the apertures can be detected as corresponding to well-defined pivotal positions (at least one) of the probe, an associated system (FIG. 8) for using the signals received by the probe can be arranged to associate each signal with a particular position of the probe so that display equipment (such as a cathode ray oscilloscope) can scan synchronously with the probe.

As an example, the apertures in the disc 17 can be arranged in a circle to co-operate with one diode pair 18 while another, single, "zero-position" aperture, radially displaced relative to the circular arrangement of apertures, can be arranged to co-operate with another diode pair 18. The signals indicating the position of the probe are thus generated several times per cycle (corresponding to the number of apertures in the circular arrangement). The spacing of the disc apertures can be non-linearly distributed in a manner such as to compensate for the variation in angle of the probe which would otherwise give rise to a non-linear relationship between signals received by the probe and their notional associated positions as determined from the encoder disc. Some of the leads 15 supply electrical power for the position-encoding means while others convey the electrical signals from the diode pairs 18.

The system shown in FIG. 8 includes a motor control unit 200, a trigger unit 201, a probe angle synthesiser 202, a rapid sector scan control unit 203, a gate 204, a camera 205 and a diasonograph D whose outline is shown in broken line. The diasonograph can be of the type available from Nuclear Enterprises Limited under model No. 4102. The diasonograph includes units 206, 207, 208 and 209 enabling time-position scanning, amplitude scanning, electrocardiograph triggering and display and recording of data obtained in the scanning operation. These facilities are well known as also is the use of the camera 205 to record photographically pictures which appear on an oscilloscope of the diasonograph.

The rapid scanning made available by the scanning device 1 described above can be utilised by the probe angle synthesiser 202 which with the control unit 203 can synchronise the display with the scanning by the probe 3. The gate 204 controlled by electrocardiograph trigger unit 208 enables synchronisation with heart operation when ultrasonically scanning the heart as described below. However, the system shown in FIG. 8 does not form part of this invention which is concerned only with the scanning device 1 and so the operation of the system shown in FIG. 8 will not be further described.

Figure 6:
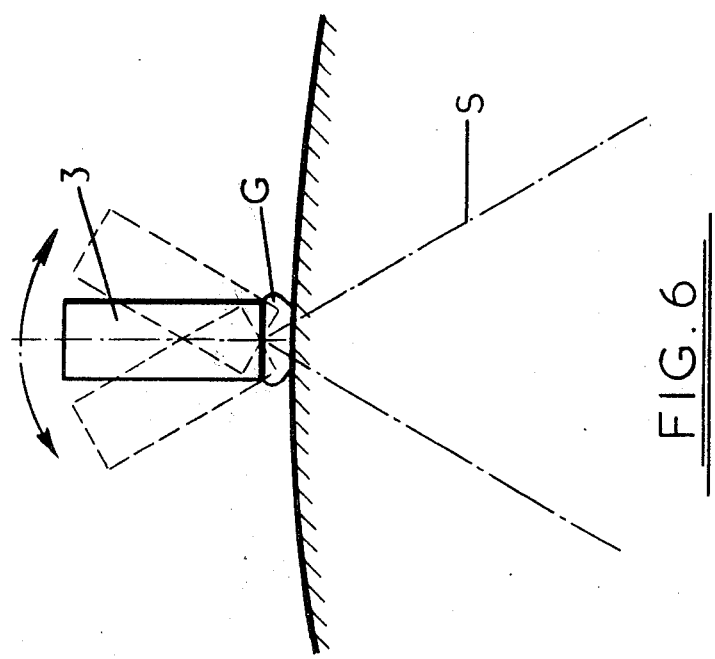

In use of the scanning device to scan a patient's heart, for example, the device 1 is placed with its tip portion in contact with the patient's skin adjacent the heart H (FIG. 7). Coupling gel G (FIG. 6) is placed between the membrane 16 and the patient's skin. The device is then operated to oscillate the probe 3 in its mounting means 5, for example, at a rate of up to 16 cycles per second, the arrangement of the cam 11 converting the rotational motion of the crank 12 into the oscillatory motion of the carriage 4.

As the probe oscillates it operates in the usual way to transmit ultrasonic signals through the patient's skin towards the heart H and to receive the echoes due to obstructions such as the heart. The echo signals are displayed and/or recorded by means of the whole or selected parts of the system (FIG. 8) synchronised with the scanning probe by means of the encoder disc 17 and photo-diode arrangement 18.

During scanning, the transmission and reception of ultrasonic pulses is so fast relative to the rate of movement of the probe that little or no allowance need be made for movement of the probe. However, the movement of the probe can be sufficiently fast to be able to provide "moving pictures" of an organ, such as the heart, in operation. For example, the operation of heart valves can be viewed (in one plane) with faults of small time-duration being rendered detachable by an observer watching an oscilloscope.

As is illustrated in FIG. 7 by arranging the probe 3 to pivot about the centre of its surface 6 the frame of reference of the transmission/reception geometry can be well defined so that measurements can readily be made accurately from the resulting display. Also, by arranging the surface 6 as close as possible to the patient's skin a well-defined sector S of the patient's body inside the skin can be covered without hindrance from obstructions such as ribs R (FIG. 7). The device 1 can be readily rotated about its longitudinal axis to alter the sector scanned while maintaining a common reference base line BB.

It is to be noted that by arranging the mounting means (plates 5, 5' etc) and moving means (gearing 13 and motor 14) as shown in the drawings, an elongate device having a housing tapered at the scanning end is obtained. In particular, the tapered scanning end portion, which can be seen to be no greater in end area than is essential for providing the "window," enables an operator to manoeuvre the device readily so that scanning between obstructions such as ribs is facilitated since the operator knows precisely where the operative window is located. The elongation of the device rather than having a lateral spread enables an operator to see more easily where he is positioning the probe.

Thus the device and system described above can provide substantially real time displays of sectors of a patient's body, which is highly desirable if attempts are to be made to measure moving parts of the patient's body or to obtain two-dimensional views quickly and conveniently. Also, the resolution of the apparatus can be altered readily to suit the needs of a particular application, as will be understood by those skilled in the art.

Clearly the device 1 (except for the probe 3) has application in scanning using various ultrasonic frequencies which can be obtained by interchanging the probe 3 with another probe or by interchanging sub-assemblies in the modified embodiment described above.

What is claimed is:

1. An ultrasonic scanning device for use in examining a mass by the transmission and reception of ultrasonic signals, comprising a housing having a window, and a thin, ultrasonically transparent flexible plastic stretched membrane secured across said window to provide a window closure, mounting means secured within the housing, an ultrasonic transmission/reception probe within the housing and mounted in the mounting means so as to face said window closure, ultrasonic coupling means between the probe and the window closure and means for moving the probe, said ultrasonic coupling means including a coupling fluid and a rolling diaphragm sealingly secured to the probe and to the housing around said window to sealingly enclose a window space between the probe and the membrane, the coupling fluid filling the window space and being confined by the diaphragm between the probe and the membrane, the mounting means constraining the probe so that the latter can effect a pivoting movement relative to the housing only in a plane through said window closure and the moving means being arranged to oscillate the probe rapidly between extreme positions of said planar pivoting movement to provide real-time scanning, the ultrasonic coupling means being arranged to deform with oscillating movement of the probe such that the window closure can be kept stationary relative to the surface of the mass being examined while the probe is oscillated rapidly in a desired plane while transmitting and receiving ultrasonic signals through said window closure to achieve real-time scanning of the mass being examined.

2. An ultrasonic scanning device according to claim 1 wherein means are provided for generating electrical signals indicative of the position of the probe relative to said mounting means, said generating means being arranged to produce said signals at a plurality of instants during each cycle of the probe's oscillatory pivoting motion.

3. An ultrasonic scanning device according to claim 1 wherein a sub-assembly of the device comprises a removable window portion of the housing, the membrane secured across the window portion, the rolling diaphragm secured to the window portion, the probe secured to the rolling diaphragm and the coupling fluid filling said window space, whereby the sub-assembly can be removed from the device and replaced by another such sub-assembly.

4. An ultrasonic scanning device according to claim 1, wherein a carriage carries the probe and the mounting means comprises an arcuate track, bearings of the carriage being provided to enable the carriage and probe to run along the track, an end face of the probe having its centre maintained in a substantially constant position about which the end face pivots.

5. An ultrasonic scanning device according to claim 1 wherein said moving means includes drive means and a push fit interconnection enabling division of the moving means into two parts associated with the probe and with the drive means respectively.

6. An ultrasonic scanning device according to claim 1 wherein said housing has an upper housing portion and a sub-assembly which can be detached from the upper housing portion and comprises the window, the mounting means, the probe and the associated part of the moving means.

7. An ultrasonic scanning device according to claim 1, and comprising a tapered end portion of the housing whose end face provides said window, the probe, mounting means and moving means being arranged in line within the housing which is elongate.

8. An ultrasonic scanning device for use in examining a mass by the transmission and reception of ultrasonic signals, comprising a housing having an ultrasonically transparent window closure, mounting means secured within the housing, an ultrasonic transmission/reception probe within the housing and mounted in the mounting means so as to face said window closure, deformable ultrasonic coupling means secured to the probe and to the housing so as to be confined between the probe and the window closure and means for moving the probe, the mounting means constraining the probe so that the latter can effect a pivoting movement relative to the housing only in a plane through said window closure, a carriage carrying the probe and the mounting means comprising an arcuate track, bearings of the carriage being provided to enable the carriage and probe to run along the track, an end face of the probe having its centre maintained in a substantially constant position about which the end face pivots, and the moving means being arranged to oscillate the probe rapidly between extreme positions of said planar pivoting movement to provide real-time scanning, an electrical lead carrying electrical signals to and from the probe extends laterally from the carriage, a spirally wound flexible tube having one end secured to the carriage and the other end secured to the mounting means, the electrical lead extending slidably through the flexible tube to a terminal of the lead via which external connection to the probe can be made, the spiral formed by the flexible tube serving to inhibit fatigue of the lead due to flexing, the ultrasonic coupling means being arranged to deform with oscillating movement of the probe such that the window closure can be kept stationary relative to the surface of the mass being examined while the probe is oscillated rapidly in a desired plane while transmitting and receiving ultrasonic signals through said window closure to achieve real-time scanning of the mass being examined.

9. An ultrasonic scanning device for use in examining a mass by the transmission and reception of ultrasonic signals, comprising a housing having an ultrasonically transparent window closure, mounting means secured within the housing, an ultrasonic transmission/reception probe within the housing and mounted in the mounting means so as to face said window closure, deformable ultrasonic coupling means secured to the probe and to the housing so as to be confined between the probe and the window closure and means for moving the probe, the mounting means constraining the probe so that the latter can effect a pivoting movement relative to the housing only in a plane through said window closure and the moving means being arranged to oscillate the probe rapidly between extreme positions of said planar pivoting movement to provide real-time scanning, said moving means including a motor, a crank connected to the motor, a rolling member pivotably connected to the crank, a carriage carrying the probe and a guide portion of the carriage which the rolling member engages, the carriage being mounted in said mounting means so as to enable said planar pivoting movement of the probe, the rolling member being arranged to roll within said guide portion along an arcuate path defined by the guide portion in a plane of the carriage transverse to the direction of movement of the carriage relative to the mounting means, the motor being arranged to rotate the crank causing in turn the rolling member to roll in said guide portion of the carriage while inducing said planar pivoting movement of the carriage and probe, the ultrasonic coupling means being arranged to deform with oscillating movement of the probe such that the window closure can be kept stationary relative to the surface of the mass being examined while the probe is oscillated rapidly in a desired plane while transmitting and receiving ultrasonic signals through said window closure to achieve real-time scanning of the mass being examined.

10. An ultrasonic scanning device according to claim 9 wherein encoding means are provided for generating electrical signals indicative of the rotational position of the crank, said encoding means including photo and light-emitting diode pairs and an encoding disc having apertures, the encoding disc being connected to the crank to rotate with the latter, the apertures of the encoding disc being arranged to pass between the diodes of each photo-light emitting diode pair.

* * * * *